United States Patent [19]

Pató

[11] 4,075,355
[45] Feb. 21, 1978

[54] METHOD AND APPARATUS FOR REGULATING THE FAT CONTENT OF MILK

[75] Inventor: Tibor Pató, Bern, Switzerland

[73] Assignee: Gebruder Ott A.G., Worb, Switzerland

[21] Appl. No.: 699,859

[22] Filed: June 25, 1976

[30] Foreign Application Priority Data

July 4, 1975 Switzerland .......................... 8782/75
May 26, 1976 Switzerland .......................... 6652/76

[51] Int. Cl.² ............................................... A23C 9/14
[52] U.S. Cl. ..................................... 426/231; 426/491
[58] Field of Search ................... 426/231, 491; 23/231; 137/625.28, 110; 73/196

[56] References Cited

U.S. PATENT DOCUMENTS

| | | | |
|---|---|---|---|
| 2,264,665 | 12/1941 | Hall | 426/231 |
| 2,567,898 | 9/1951 | Staaff | 426/231 |
| 3,829,584 | 8/1974 | Seiberling | 426/231 |
| 3,983,257 | 9/1976 | Malmberg et al. | 426/231 |

*Primary Examiner*—Hiram H. Bernstein
*Attorney, Agent, or Firm*—Michael J. Striker

[57] ABSTRACT

A method and apparatus for regulating the fat content of milk, including that of cream, by separating whole milk into skim milk and cream, mixing part of the cream with the skim milk, determining the respective densities of the skim milk and of the mixture, and controlling the mixture ratio as a function of the difference between these densities by means of an electronic control unit connected to a dosing pump. The fat content of cream may also be regulated by using a pressure control valve, and the fat content of milk intended for cheese production may be regulated in proportion to the nonfat solids content.

14 Claims, 10 Drawing Figures

METHOD AND APPARATUS FOR REGULATING THE FAT CONTENT OF MILK

BACKGROUND OF THE INVENTION

This invention relates to a method and apparatus for regulating the fat content of milk, of the type wherein whole milk is separated into a nonfat component and a fatty component, and part of the fatty component is then re-added to the nonfat component to form a mixture.

An article entitled "Milchstandardisierung: Herstellung von Milch mit einem bestimmten Fettgehalt," by H. Niemeyer, in *Deutsche Milchwirtschaft* 26(8) of 19 Feb. 1975, describes various methods of producing milk having a specific fat content. In most of the known methods, the raw product, i.e., the whole milk, is separated in a separator into a nonfat component and a fatty component, e.g., skim milk and cream. These two components are stored in separate tanks, and after determination of the fat content of the whole milk and of the fatty component obtained by means of the separator, a predetermined amount of either the fatty or the nonfat component is mixed into whole milk, making the end product, i.e., the so-called standardized milk, lower or richer in fat.

Another method is to separate the whole milk in a separator into a nonfat and a fatty component, roughly adjusting the fat content of the fatty component to any desired value by inserting volume limiters. After the separator, part of the fatty component is first re-added to the nonfat component according to the desired fat content of the end product. The rest of the fatty component is led off and stored in a separate tank. The mixture having a roughly adjusted fat content is likewise stored in another tank. After determination of the fat content of the mixture, of the raw product, and of the fatty component, the fat content of the end product, i.e., of the standardized milk, is corrected by addition of either nonfat or fatty component.

The drawback of these two known methods is that an extensive tank installation is needed, that processing is relatively time-consuming, and that a long delay is unavoidable between reception of the whole milk and processing, i.e., production of the standardized milk. The fat content of the whole milk, or the nonfat and fatty components, and of the standardized milk is determined by taking samples which are tested for their fat content in a laboratory.

Fully-automatic adjustment of the fat content of milk has also already been proposed. According to one fully-automatic method, after the whole milk has been separated into a nonfat and a fatty component, the density of the nonfat component, which density is dependent upon the fat content, is measured by means of a hydrometer. According to the result of this determination of the fat content, a dosing member is triggered via a computer and supplies to the nonfat component an amount of the fatty component corresponding to the desired fat content of the end product. In this method, the fat content of the resultant product is not measured directly. Inasmuch as density is dependent upon temperature, temperature fluctuations bring about wide variations in the measured fat content even though there is no significant change in the actual fat content.

In another known fully-automatic method, the fat content of the standardized milk is determined by means of a special measuring device. First the whole milk is separated in a separator into skim milk and cream, and then part of the cream is re-added to the skim milk via a dosing member. After mixing, a sample is automatically withdrawn every half-minute, the fat content of this sample is automatically determined with the aid of the special measuring device, and the dosing member is readjusted according to the result of this measurement. The fat content is determined according to the principle of light-dispersion measurement by a very sensitive measuring element which is exposed to the rather rough conditions of normal dairy operation and is often damaged. Measurement does not take place continuously but at intervals, so that incorrect adjustment is quite possible during the intervals. Moreover, the measuring device must be frequently recalibrated if the fat content of the standardized milk is not to vary too much from the specified norm. Finally, the cleaning of this measuring device entails certain problems, and readjustment is necessary after cleaning.

SUMMARY OF THE INVENTION

It is an object of this invention to provide a method and apparatus for regulating the fat content of milk which make it possible to split whole milk up directly, i.e., without prior treatment thereof, into standardized milk and a fatty component, the fat content of the standardized milk being adhered to much more accurately than is the case with the known methods.

A further object of this invention is to provide apparatus which is of simpler and sturdier construction, and which is consequently cheaper to manufacture, than prior art apparatus.

To this end, the improved method according to the present invention comprises the steps of determining the respective densities of the nonfat component and of the mixture of the nonfat component and part of the fatty component, and controlling the mixture ratio of the mixture as a function of the difference between those densities.

In the apparatus for carrying out the foregoing method according to the present invention, in which whole milk is separated into a nonfat component and a fatty component by means of a separator having a first outlet for the nonfat component and a second outlet for the fatty component, and in which part of the fatty component is then mixed with the nonfat component by controllable mixing means having at least two inlets and one outlet and connecting the second separator outlet with the first separator outlet, the improvement comprises a first densimeter disposed between the first separator outlet and one of the mixing means inlets for determining the density of the nonfat component, a second densimeter disposed at the mixing means outlet for determining the density of the mixed components, and electronic control means for controlling the mixture ratio of the mixed components as a function of the difference between the respective densities determined by the first and second densimeters.

BRIEF DESCRIPTION OF THE DRAWING

Preferred embodiments of the invention will now be described in detail with reference to the accompanying drawings, in which.

SPECIFIC DESCRIPTION OF PREFERRED EMBODIMENTS

Figure 1:
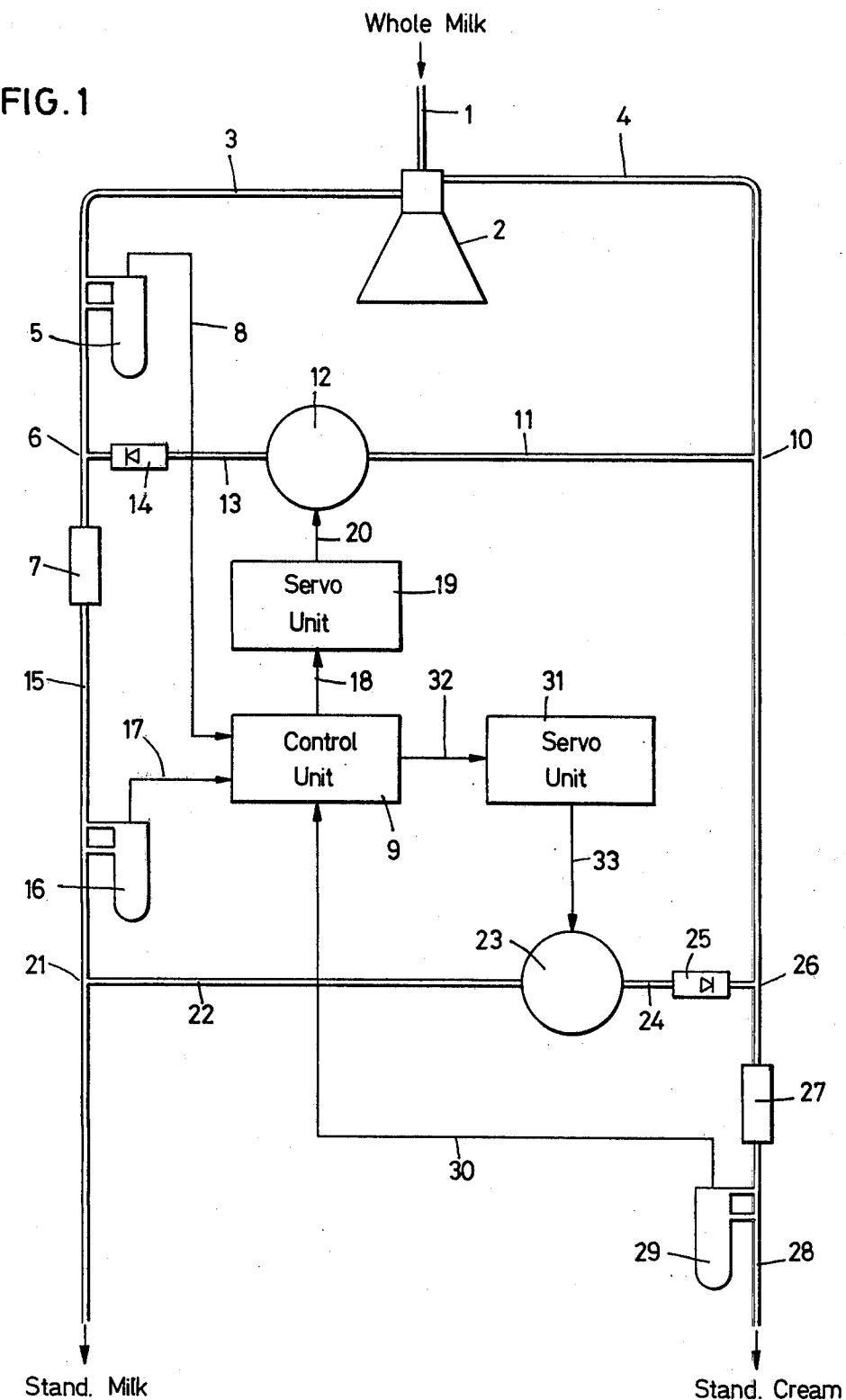
FIG. 1 is a diagram of apparatus according to a first embodiment of the invention, with pipes for conveying milk or components thereof being shown as double lines and wires for conveying electric signals being shown as single lines.

In the apparatus for regulating the fat content of milk as illustrated diagrammatically in FIG. 1, whole milk received is supplied through a pipe 1 to a separator 2, where it is separated into a nonfat component, i.e., skim milk, and a fatty component, i.e., cream. The skim milk leaves the separator 2 through a pipe 3, and the cream is led off through a pipe 4.

The skim milk flows via a densimeter 5 to a T-piece 6 of the pipe 3 and on into a mixer 7. As a function of the density of the skim milk, the densimeter 5 produces an electric signal which is supplied over a line 8 to a first input of a control unit 9.

The cream flows through the pipe 4 to a branching-off point 10, from which part of the cream is conveyed through a pipe 11 to a dosing pump 12. From the outlet of the dosing pump 12, the cream flows in measured quantities through a pipe 13, a check valve 14, and T-piece 6 into the skim milk. After the T-piece 6, the nonfat and fatty components, i.e., the skim milk and the measured quantities of cream, flow into the mixer 7, in which the cream is thoroughly mixed with the skim milk to yield a homogeneous, standardized milk product having the desired fat content. From the mixer 7, the standardized milk flows through a pipe 15 to a further densimeter 16 which produces, as a function of the density of the standardized milk, an electric signal which is supplied over a line 17 to a second input of the control unit 9.

As a function of the difference between the signals produced by the densimeters 5 and 16, the control unit 9 generates a control signal which is supplied over a line 18 to a servo unit 19 which generates a regulating signal for the dosing pump 12, this regulating signal being supplied to the dosing pump 12 over a line 20.

Standardized milk may be withdrawn from the pipe 15 after the densimeter 16, and cream with a high but undetermined fat content may be withdrawn from the pipe 4 after the branching-off point 10.

For the purpose of standardizing the fat content of the cream as well, the apparatus further comprises a branching-off point 21 in the pipe 15. From the branching-off point 21, part of the standardized milk flows through a pipe 22 to a further dosing pump 23 and through a pipe 24, a check-valve 25, and a T-piece 26 in the pipe 4 into the cream. The pipe 4 opens out after the T-piece 26 into a further mixer 27 in which the cream and the part of the standardized milk added to the cream are thoroughly mixed. Connected to the outlet of the mixer 27 is a pipe 28 for withdrawing the standardized cream. Inserted in the pipe 28 is a third densimeter 29 for producing a signal dependent upon the density of the standardized cream, which signal is likewise supplied, over a line 30, to the control unit 9. In this case, the control unit 9 is further designed to generate, as a function of the difference between the signals supplied by the densimeters 5 and 29, a further control signal for an additional servo unit 31, this control signal being supplied to the servo unit 31 over a line 32. The servo unit 31 generates a regulating signal which is supplied to the dosing pump 23 over a line 33.

The great advantage of the apparatus described above with reference to FIG. 1 is that the whole milk received can be conveyed to the apparatus directly and without delay through the pipe 1 and that the standardized milk can be withdrawn from the pipe 15 and the standardized cream from the pipe 28. No tanks are necessary for separate intermediate storage of the nonfat and fatty components.

The fat content is determined by measuring the densities of the skim milk and the end products. The density depends not only on the fat content alone, but also on the nonfat solids, such as protein, milk sugar, minerals, etc., and on the temperature. By measuring the density of the nonfat component, i.e., the skim milk, as well as the densities of the standardized milk and standardized cream, and by establishing the differences between these measurements, the above-mentioned factors are eliminated except for the fat content, so that practically speaking, the difference in the measured values depends only upon the difference between the fat content of the skim milk and that of the standardized milk or cream. Since the only difference between the product flowing through the pipe 15 and that flowing through the pipe 3 is that part of the fatty component has been added, the densities determined by the densimeters 5 and 16 differ only as regards the fat content. The influence of the nonfat solids and of the temperature is eliminated because the solids derive from the same raw product and the temperature is substantially the same in both densimeters.

Figure 2:
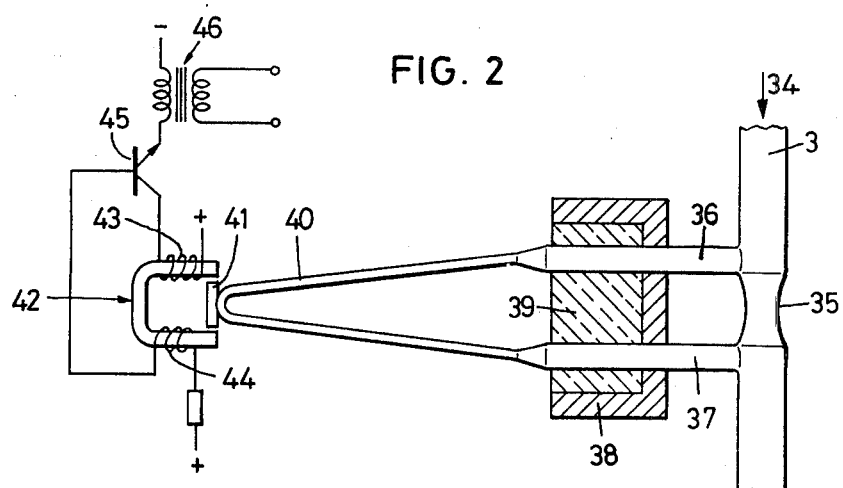
FIG. 2 is a partly diagrammatic view of a resonator by means of which an electric signal is generated, the frequency of which signal is dependent upon the density of the liquid flowing through the resonator.

FIG. 2 shows the contruction of a densimeter, e.g., the densimeter 5, in greatly simplified form by way of a diagram. The skim milk flows in the direction of an arrow 34 through the pipe 3, which has a constricted portion 35, so that part of the skim milk enters the densimeter through an inlet pipe 36 and, after passing through the densimeter, flows back into the pipe 3 through an outlet pipe 37 situated after the constricted portion 35. The inlet pipe 36 and the outlet pipe 37 pass through a cup-like housing 38 in which they are embedded by means of a plastic mass 39 which holds them rigidly. The ends of the pipes 36 and 37 projecting beyond the mass 39 are tapered and are interconnected by a V-shaped tube 40. The pipes 36 and 37 and the tube 40 are preferably made of glass. Rigidly secured at the bend of the tube 40 is a permanently magnetized bar 41. The tube 40 and the magnetized bar 41 together form a flexural resonator, the bar 41 being able to oscillate along a straight line perpendicular to the drawing plane of FIG. 2 when excited by means of an electromagnet 42 comprising a drive winding 43 and a control winding 44. A positive voltage is supplied via the drive winding 43 to the collector of a transistor 45. The feedback signals induced in the control winding 44 reach the base of the transistor 45. The collector of the transistor 45 is connected via the primary winding of a transformer 46 to the negative terminal of a voltage source (not shown). The flexural resonator comprising the tube 40 and the permanent magnet 41, plus the electromagnet 42 and the transistor 45, form an oscillator which produces an AC-voltage electric signal, the frequency of which is dependent upon the natural frequency of the flexural resonator. This signal is picked up at the secondary winding of the transformer 46 and supplied to the control unit 9, e.g., over the line 8, as shown in FIG. 1. The natural frequency of the flexural resonator depends upon the density of the skim milk flowing through the tube 40 and may, for example, be from 200 to 500 Hz. Thus the data concerning the ascertained density are contained in the frequency of the signal picked up at the secondary winding of the transformer 46 and not in the voltage of that signal. The lines 8, 17, and 23, over which the signals are supplied to the control unit 9, may be of any desired length, the data content not being affected by the attenuation occurring in these lines. Hence the control unit 9 may be set up at some distance from the remainder of the apparatus without any resultant disturbance in the functioning of the measurement procedure.

Figure 3:
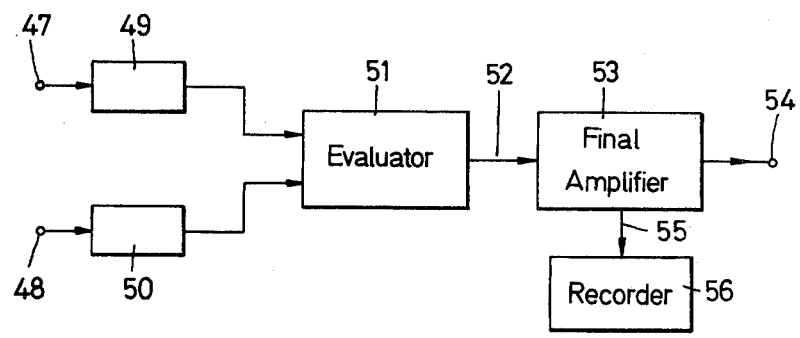
FIG. 3 is a block diagram of a control unit which produces a regulating signal for a dosing pump as a function of the signals generated by the resonators.

FIG. 3 is a block diagram of a first version of the control unit 9. The signal produced by the densimeter 5 is supplied to a first input 47 and the signal produced by the densimeter 16 to a second input 48. The signals reaching the inputs 47 and 48 are preferably harmonic AC voltages, the frequencies of which are, as mentioned above, dependent upon the density of the liquids flowing through the respective densimeters, they are supplied to limiters 49 and 50, respectively. At the output of each limiter there appears a sequence of rectangular pulses of constant amplitude, the pulse sequence frequency of which corresponds to the frequency of the respective signal. The rectangular pulses are fed to an evaluation circuit 51, at the output of which appears an analog output signal proportional to the difference between the pulse sequence frequencies of the rectangular pulse sequences supplied to the evaluator 51. For example, a differentiator (not shown) may be associated with each input of the evaluation circuit 51, which differentiator produces a measurement pulse of constant amplitude and constant duration each time the leading or the trailing edge of each rectangular pulse arrives. A capacitor (not shown) is charged by these measurement pulses. Since the pulse sequences of the measurement pulses exactly correspond to the pulse sequences of the rectangular pulses, the number of measurement pulses reaching the capacitor per unit of time is proportional to the frequency of the signal produced by the respective densimeter. Consequently, the voltage to which the capacitor is charged is also proportional to the frequency of that signal. By subtracting the charging voltage of the capacitor charged by the signal at the input 47 from the charging voltage of the capacitor charged by the signal at the input 48, the above-mentioned analog output signal is obtained, which is supplied over a line 52 to a final amplifier 53 for producing the analog control signal. The control signal leaves the control unit 9 via an output terminal 54 and reaches the servo unit 19 over the line 18 (FIG. 1). The final amplifier 53 comprises a further decoupled output connected via a line 55 to a recorder 56. In the recorder 56, the value of the control signal is recorded for monitoring the operation of the apparatus. Furthermore, the evaluation circuit 51 contains means (not shown) for adding an adjustable additional voltage to the above-mentioned differential voltage between the charging voltages of the capacitors in order to obtain the analog output signal. The magnitude of this additional voltage determines the fat content of the standardized milk and may be adjusted accordingly.

Figure 7:
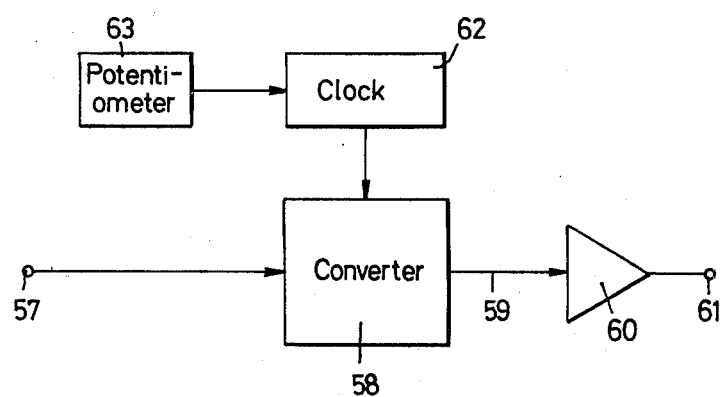
FIG. 7 is a block diagram of a servo unit controlling the dosing pump of FIGS. 4 and 5 as a function of the regulating signal.

A block diagram of the servo unit 19 is shown in FIG. 7. The analog control signal is supplied over the line 18 to an input 57, reaches a converter 58, and is converted therein into pulses having a constant pulse sequence and of an amplitude proportional to the control signal. These pulses are supplied over a line 59 to a power amplifier 60, at the output 61 of which a pulsed regulating signal appears, which reaches the dosing pump 12 over the line 20. The constant pulse frequency is generated by a clock 62 and can be adjusted by means of a potentiometer 63.

The servo unit 19 may also be designed in such a way that the number of pulses of the regulating signal varies proportionally to the analog control signal, whereby the amplitude of these pulses is not changed, however. By means of the potentiometer 63, the amplitude of the pulses of the regulating signal can then be influenced.

Figure 4:
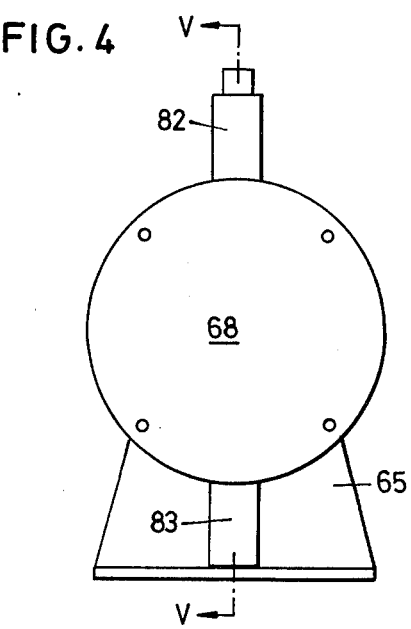
FIG. 4 is an elevation of a simple dosing pump.
Figure 5:
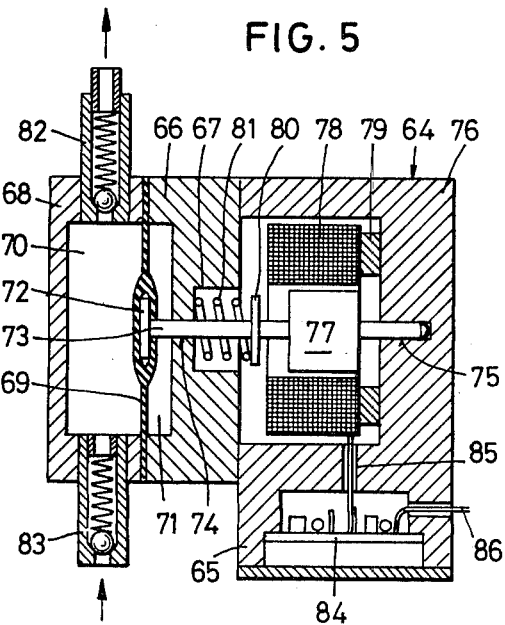
FIG. 5 is a section taken on the line V—V of FIG. 4.

Illustrated in FIGS. 4 and 5 is a simple version of a pump suitable for use as the dosing pump 12 or 23. This pump comprises a cylindrical housing 64 having a hollow base 65. The opening into the housing 64 is closed off by a disc 66 having an axially extending rim. The disc 66 and a cover 68, also having an axially extending rim, together enclose a chamber which is divided into a working space 70 and an interspace 71 by an elastic diaphragm 69, the edge of which is gripped between the rim of the disc 66 and the rim of the cover 68.

Embedded in the central portion of the diaphragm 69 is a plate 72 of a driving rod 73. The driving rod 73 extends through a bore 74 in the center of the disc 66 and through a recess in the disc 66 and projects into a blind-end bore 75 in the back 76 of the housing 64. Secured to the part of the rod 73 passing through the interior of the housing 64 is a cylindrical body 77 of a ferromagnetic material. Disposed coaxially about the body 77 is a coil 78 which is rigidly connected to the back 76 of the housing 64 via a spacer ring 79. The connecting wires of the coil 78 are led through a channel 85 in the wall of the housing 64 and extend into the hollow base 65. Between the plate 72 and the body 77, a split thrust ring 80 is held in a groove of the rod 73. The ends of a spring 81 rest against the disc 66 and the thrust ring 80, respectively; the spring 81 presses the rod 73 against the back of the blind-end bore 75, with this back serving as a stop.

When the coil 78 is excited, the ferromagnetic body 77 moves to the left, as viewed in FIG. 5, and thus the driving rod 73 is likewise pushed to the left against the return force of the spring 81. By means of the plate 72, the diaphragm 69 is bulged out towards the left, thereby reducing the volume of the working space 70. Part of the cream or milk in the working space 70 leaves that space via a check valve 82 disposed on the upper side of the rim of the cover 68. The quantity expelled is dependent upon the distance travelled by the rod 73. When the current passing through the coil 78 is interrupted, the rod 73 is returned to its starting position by the spring 81, so that the diaphragm 69 likewise moves back into its original position. Thus the volume of the working space 70 is again increased, and more cream or milk is enabled to enter the working space 70 through a second check valve 83. The quantity of cream or milk delivered during a given period of time depends upon the intensity of the current exciting the coil 78, on the one hand, and upon the number of pulses supplied to the coil 78 during that period of time, on the other hand.

The servo unit illustrated in FIG. 7 is preferably mounted on a printed wiring board disposed within the base 65 of the dosing pump shown in FIGS. 4 and 5. The connecting wires for the coil 78 represent the line designated as 20 in FIG. 1, over which the pulsed regulating signal is supplied to the dosing pump. The control signal reaches the servo unit over lines 86, corresponding to the line 18.

Figure 6:
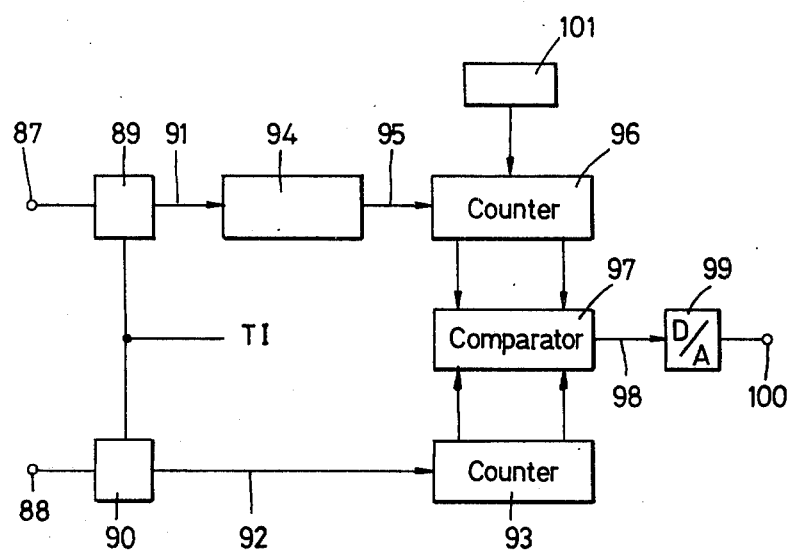
FIG. 6 is a block diagram of a digitally operating control unit.

FIG. 6 is a block diagram of a digitally operating control unit. The signals produced by the densimeters 5 and 16 are supplied to inputs 87 and 88, respectively, and thence to respective gates 89 and 90. Timing pulses TI are also supplied to the gates 89 and 90, e.g., a timing pulse TI of 50 ms duration every half-second. In each of these gates there is a counter (not shown) which counts the positive half-waves, occurring between two successive timing pulses TI, of the signals produced by the respective densimeters. The counter readings attained upon the occurrence of each timing pulse are coded, and the coded counter readings are transmitted in parallel form over respective multiple lines 91 and 92. The coded information derived from the densimeter 16 reaches a counter 93 directly over the multiple line 92. The information derived from the densimeter 5 reaches a shift register 94 over the multiple line 91, is stored in the shift register 94, and is passed on to a counter 96 with delay over a multiple line 95. The length of the delay with which the information is passed on to the counter 96 corresponds to the time required for a particle of skim milk to travel from the densimeter 5 through the T-piece 6 and the mixer 7 to the densimeter 16. As a result, the densities of the standardized milk are taken into account in determining the fat content. The information which simultaneously reaches the counters 93 and 96 corresponds to the densities of a portion of the skim milk and of the mixture of this portion of the skim milk with cream. Each time information is taken up in the counters 93 and 96, the counter readings thereof are thereupon immediately compared by means of a comparator 97. The difference between the readings of the counters 93 and 96 appears at the output of the comparator 97 in digitally coded form. This coded differential signal is supplied over a multiple line 98 to a digital-to-analog converter 89, at the output 100 of which the analog control signal appears which is supplied to the servo unit 19 over the line 18.

To eliminate the influence of the temperature upon the determination of the densities, it is preferable to have the densimeters 5 and 16, and possibly the densimeter 29 as well, accommodated in a single housing.

By introducing a correction value, corresponding to the difference between the fat content of the skim milk and that of the standardized milk, into the counter 96 by means of a potentiometer 101, the analog control signal at the output 100 is altered in such a way that via the dosing pump 12, enough cream is re-added to the skim milk so that the fat content of the standardized milk corresponds to the desired value.

The apparatus described above functions properly only when the fat content of the whole milk is higher than that of the standardized milk. If this is not the case, additional cream should be introduced into the pipe 4 from a cream reservoir (not shown).

The fat content of the standardized cream is regulated in basically the same way as that of the standardized milk. The control unit 9 comprises an additional limiter for converting the harmonic signal produced by the densimeter 29 into rectangular pulses. The difference between the data concerning the density of the skim milk and that of the standardized cream is ascertained in an additional evaluator and supplied as an analog output signal to an additional final amplifier which generates the control signal for the servo unit 31 controlling the dosing pump 23.

One advantage of the apparatus described above with reference to FIG. 1 is that the fat content of the standardized milk and that of the standardized cream can constantly be regulated simultaneously. The whole milk can be processed very rapidly, and the respective fat contents are regulated more accurately than with known apparatus. Thus the apparatus described here is significantly more economical. Cleaning presents no problems, and since the density measurements are not absolute but only relative to one another, adjustment of the densimeters is considerably more simple.

Figure 8:
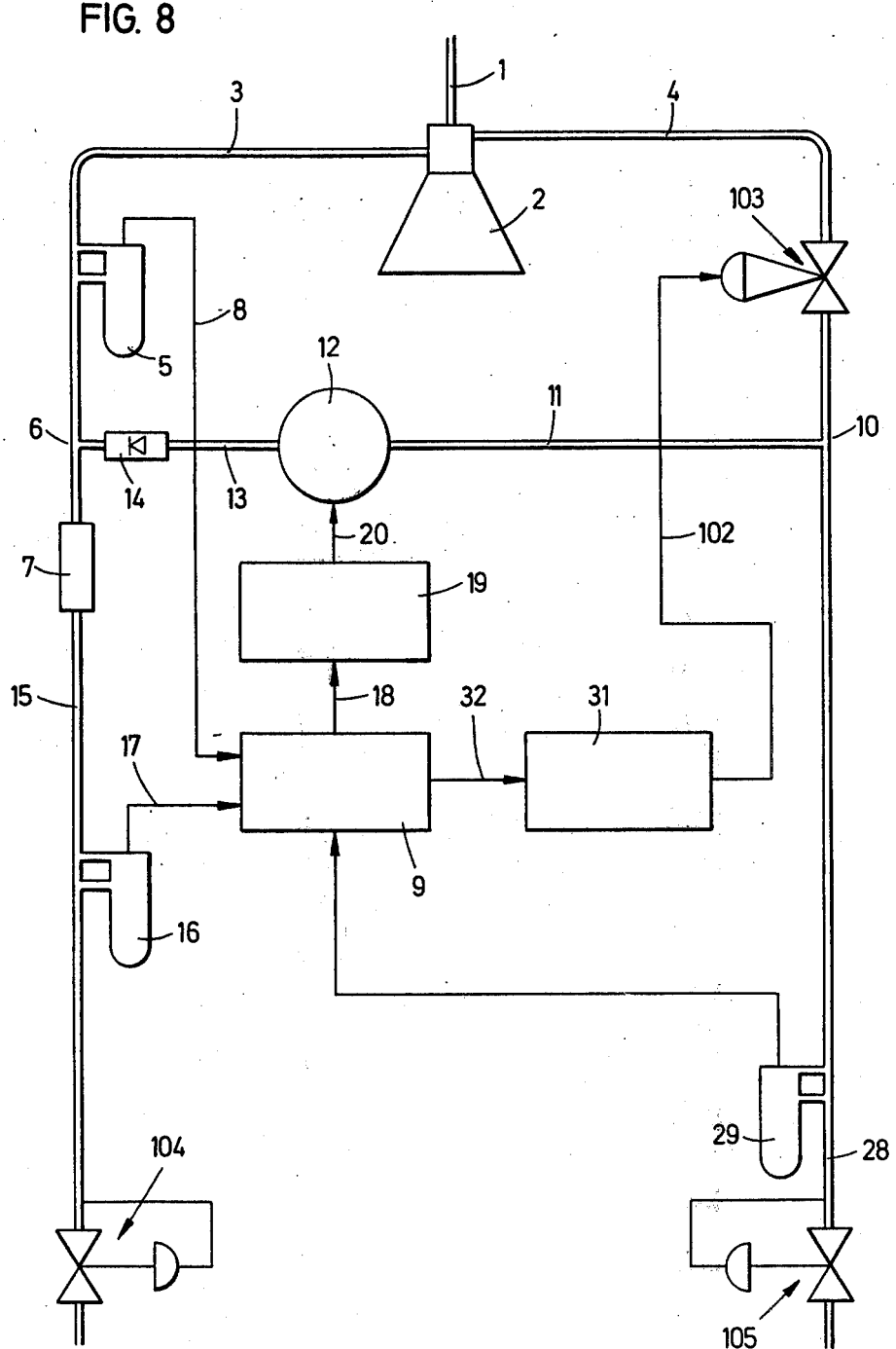
FIG. 8 is a diagram of a second embodiment of apparatus according to the present invention.

The apparatus illustrated in FIG. 8 differs from that shown in FIG. 1 only in the manner in which the fat content of the standardized cream is regulated. Those parts which perform the same functions as in FIG. 1 are designated by the same reference numerals. The whole milk conveyed to the separator 2 through the pipe 1 is separated therein into the nonfat component, which leaves the separator 2 through the pipe 3, and the fatty component, which leaves the separator 2 through the pipe 4.

The densities of the nonfat component before and of the mixture after the mixer 7 are measured in the same way as in the apparatus of FIG. 1 by means of the densimeters 5 and 16 for the nonfat component and the standardized milk, respectively, and the density of the standardized cream is measured with the aid of the densimeter 29. The output signal generated by the servo unit 31 is supplied over a line 102 to a pressure control valve 103 disposed in the pipe 4 before the branching-off point 10. Since the fat content of the cream which leaves the separator 2 through the pipe 4 depends upon the pressure in the pipe 4, or at the respective outlet of the separator 2, the fat content of the cream can be held constant at a desired level by means of the pressure control valve 103 and the servo unit 31. In the embodiment illustrated in FIG. 8, the dosing pump 23 and the mixer 27 of the apparatus of FIG. 1 may be dispensed with.

Pressure-stabilizing valves 104 and 105 are preferably also disposed at the respective outlets of the pipes 15 for the standardized milk and 28 for the standardized cream. This tends to steady the functioning of the apparatus inasmuch as the control operations are damped by the constant pressure in the various pipelines.

Figure 9:
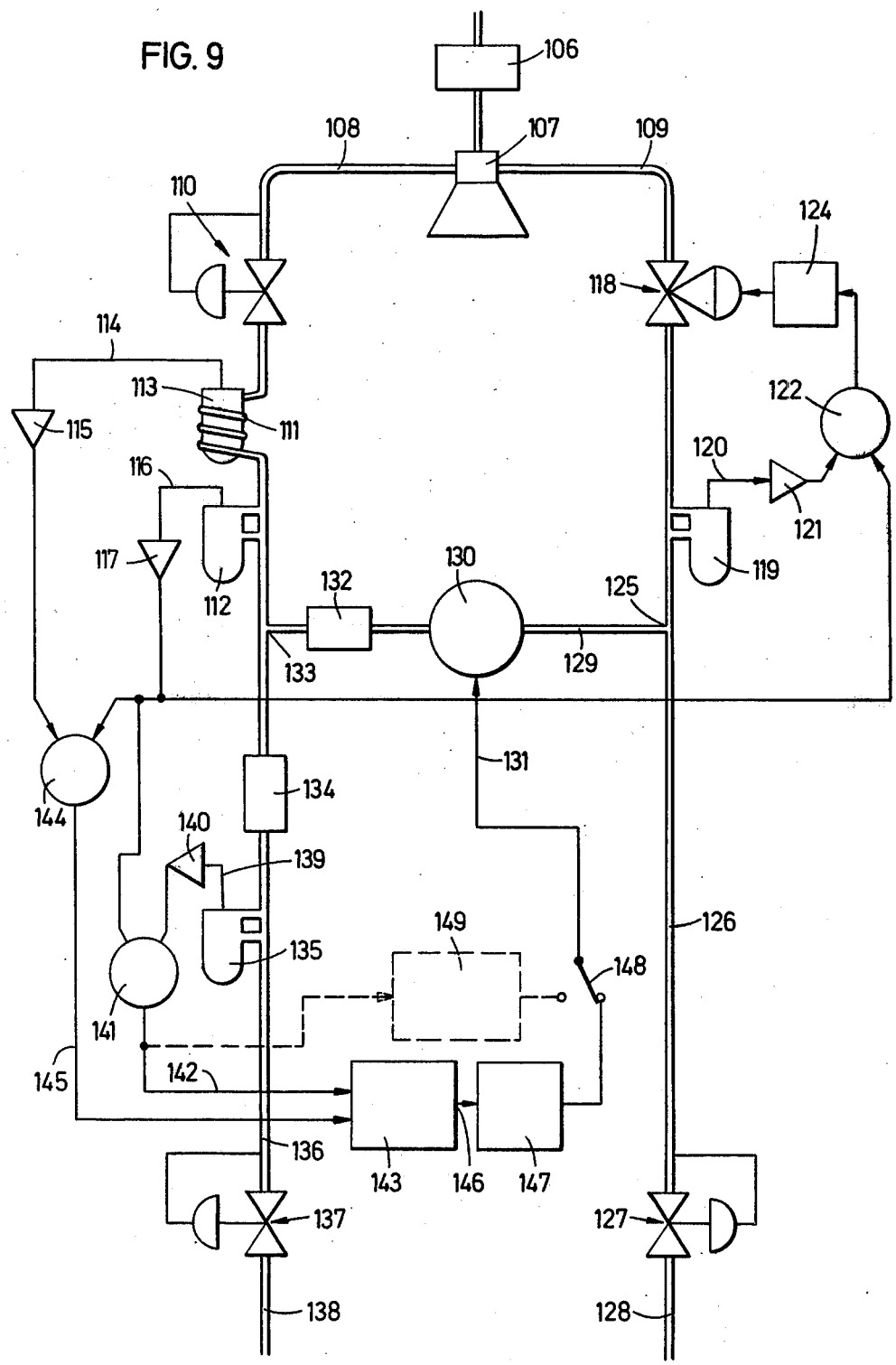
FIG. 9 is a diagram of apparatus for regulating the fat content of milk to be used in the production of cheese.

The apparatus illustrated in FIG. 9 is intended for regulating the fat content of milk for use in the production of cheese. Unlike milk for sale to consumers, where the fat content is held constant at an established level, milk for cheese production must have a fat content regulated in a predetermined ratio to the nonfat solids in the milk. As already mentioned above, these nonfat solids essentially comprise protein, mineral salts, and milk sugar. Besides the steps described above in connection with FIGS. 1 and 8 for determining the fat content and controlling the mixing of the nonfat and fatty components, additional steps are necessary for determining the solids content in order to control the mixing operation as a function of both the fat content and the solids.

In the apparatus diagrammed in FIG. 9, the whole milk is conveyed via a volume limiter 106 to a separator 107 which separates the whole milk into a nonfat component, which leaves the separator 107 through a pipe 108, and a fatty component, i.e., cream. The cream leaves the separator 107 through a pipe 109. A pressure-stabilizing valve 110 is disposed in the pipe 108. The nonfat component is then conveyed to a heat exchanger 111 and immediately thereafter reaches a densimeter 112. The heat exchanger 111 is disposed in close proximity to a reference densimeter 113 which is of essentially the same construction as the densimeter described above in connection with FIG. 2, one difference being that the inlet pipe 36 and the outlet pipe 37 are not connected to the pipe carrying the nonfat component but to each other, so that the inlet and outlet pipes 36, 37 and the V-shaped tube 40 form a closed receptacle, which is filled with distilled water. The output signal produced by the reference densimeter 113, which is supplied over a line 114 to a measuring amplifier 115, is proportional to the density of the distilled water contained in the mentioned receptacle. The heat exchanger 111 serves the sole purpose of ensuring that the temperature of the distilled water is the same as that of the nonfat component.

The densimeter 112 operates in exactly the same way as the densimeter 5 of the apparatus according to FIGS. 1 or 8, and the electric signal produced, which is dependent upon the density of the nonfat component, reaches a measuring amplifier 116 over a line 116.

The fat content of the cream is regulated in the apparatus illustrated in FIG. 9 in a manner similar to that of the apparatus according to FIG. 8. The cream flows through the pipe 109 into a pressure control valve 118 and then into a densimeter 119, the output signal of which, dependent upon the density of the cream, is supplied over a line 120 to a further measuring amplifier 121. The output signals of the measuring amplifier 116 and the measuring amplifier 121 are supplied to a subtractor 122 which transmits a differential signal over a line 123 to a servo unit 124, which in turn controls the pressure control valve 118 in such a way that the cream leaving the separator 107 has the uniform fat content desired.

The cream having a uniform fat content flows from the densimeter 119 to a T-piece 125 and thence either through a pipe 126 and a pressure-stabilizing valve 127 to a withdrawal point 128 for standardized cream, or through a pipe 129 to a dosing pump 130. The dosing pump 130 conveys the cream from the T-piece 125, as a function of a regulating signal supplied to the dosing pump 130 over a line 131, through a check valve 132 to a T-piece 133 in which the nonfat component and the cream in measured quantities are combined and then thoroughly mixed in a mixer 134.

After leaving the mixer 134, the nonfat component mixed with the cream in measured quantities reaches a densimeter 135 as milk having a regulated fat content, and finally flows through a pipe 136 and a pressure-stabilizing valve 137 to a withdrawal point 138 for milk suitable for cheese production. The electric signal produced in the densimeter 135, dependent upon the density of the milk having a regulated fat content, is supplied over a line 139 and via a measuring amplifier 140 to a subtractor 141, to which the amplified output signal of the densimeter 112 is also transmitted. The output signal of the subtractor 141, representing a measure of the fat content of the milk in the pipe 136, is fed over a line 142 to a ratio computer 143.

The amplified output signals of the reference densimeter 113 and of the densimeter 112 reach a subtractor 144, the output signal of which, corresponding to the proportion of nonfat solids, is likewise supplied to the ratio computer 143 over a line 145. The ratio computer 143 is designed to yield the quotient of the signals supplied to it over the lines 142 and 145 and to produce at its output 146 a control signal which is proportional to the ratio between the fat content of the milk in the pipe 136 and the proportion of nonfat solids in that milk. This control signal is supplied to a servo unit 147 which, as a function of the aforementioned ratio, generates the regulating signal supplied to the dosing pump 130 over the line 131.

The milk leaving the apparatus at the withdrawal point 138 has a fat content which bears a constant relationship to the nonfat solids therein. This milk is suitable for the production of cheese because with it, the fat content of the finished cheese can be kept at the desired level within very narrow limits.

Preferably, a change-over switch 148 is inserted in the line 131, which switch enables the regulating signal generated by a servo unit 149, shown in dashed lines, to be supplied to the dosing pump 130. The input of the servo unit 149 is connected to the output of the subtractor 141. The output signal of the subtractor 141 is dependent only upon the fat content of the milk flowing through the pipe 136, so that when the switch 141 is reversed, standardized milk having a uniform fat content flows out at the withdrawal point 138. With the apparatus illustrated in FIG. 9, depending upon the position of the switch 141 either milk suitable for cheese production or standardized milk, plus standardized cream in addition thereto, can be withdrawn.

Instead of the heat exchanger 111, the reference densimeter 113, and the measuring amplifier 115, provision may be made for a circuit arrangement (not shown), at the output of which an electric signal dependent upon the temperature of the nonfat component in the region of the densimeter 112 is produced, which signal is equivalent to the output signal of the measuring amplifier 115 and corresponds to the density of pure water having the same temperature as the nonfat component in the densimeter 112.

Figure 10:
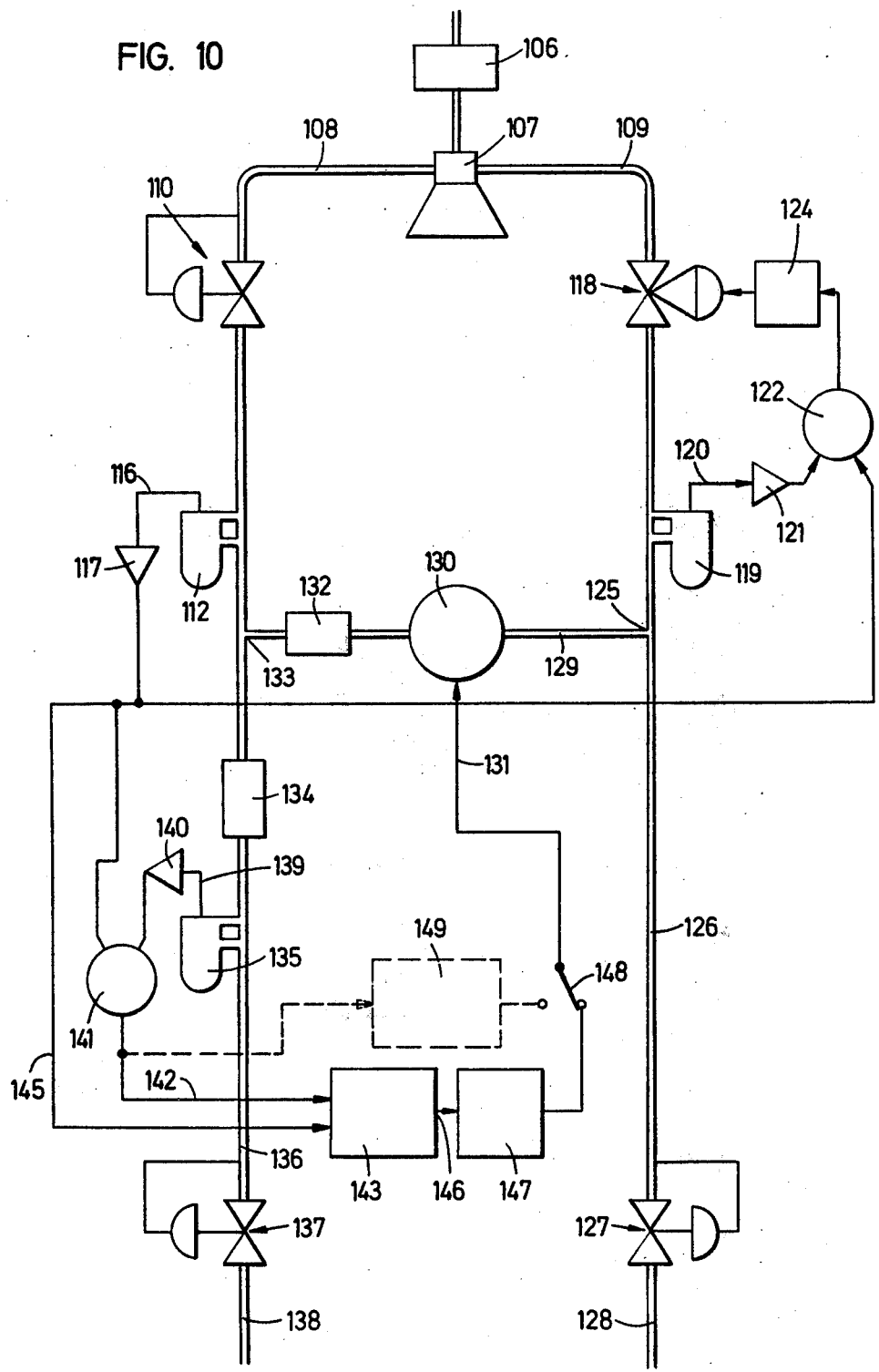
FIG. 10 is a diagram of a further embodiment of apparatus for regulating the fat content of milk to be used in the production of cheese.

The apparatus illustrated in FIG. 10 differs from that of FIG. 9 only in the way in which the density measurements of the nonfat milk component are carried out. Those parts having the same function as in the apparatus of FIG. 9 are designated by the same reference numerals.

In the apparatus according to FIG. 10, the whole milk is conveyed via the volume limiter 106 to the separator 107 which separates the whole milk into a nonfat component, which leaves the separator 107 through the pipe 108, and a fatty component, i.e., cream. The cream leaves the separator 107 through the pipe 109. The pressure-stabilizing valve 110 is disposed in the pipe 108. The nonfat component is then conveyed to the densimeter 112, which compensates for the temperature of the milk, and the electric signal produced, which is dependent upon the density of the nonfat component and thus upon the nonfat component of the milk, reaches the measuring amplifier 116 over the line 117.

The amplified output signal of the densimeter 112, corresponding to the proportion of nonfat solids, is likewise supplied to the ratio computer 143 over the line 145. The ratio computer 143 is designed to yield the quotient of the signals supplied to it over the lines 142 and 145 and to produce at its output 146 a control signal which is proportional to the ratio between the fat content of the milk in the pipe 136 and the proportion of nonfat solids in that milk. This control signal is supplied to the servo unit 147 which, as a function of the aforementioned ratio, generates the regulating signal supplied to the dosing pump 130 over the line 131.

What is claimed is:

1. A method of producing standardized milk with a given fat content from whole milk, said method comprising the steps of:
   separating said whole milk into skim milk and cream;
   passing said skim milk along a path without substantial temperature change;
   measuring at an upstream measuring location in said path the density of said skim milk and producing a skim-milk output corresponding to the measured density;
   introducing into said path at a mixing location downstream of said measuring location and mixing with said skim milk a variable portion of said cream;
   measuring at a downstream measuring location downstream of said mixing location in said path the density of the mixture of said skim milk and said variable portion of said cream and producing a mixture output corresponding to the measured density of said mixture, whereby the variation between said mixture and skim-milk outputs is substantially only indicative of the fat content of said mixture; and
   comparing said outputs and varying the size of said variable portion in dependence on the variation between said outputs so as to impart to said mixture said given fat content.

2. The method defined in claim 1, wherein said variable portion is at substantially the same temperature as said skim milk in said path.

3. The method defined in claim 2, wherein said outputs are electrical signals.

4. The method defined in claim 3, wherein said electrical signals have frequencies corresponding to the respective densities.

5. The method defined in claim 2, wherein said skim milk takes a predetermined time to travel in said path from said upstream to said downstream measuring location, said method further comprising the step of delaying said skim-milk output for substantially said predetermined time before comparing same with said mixture output.

6. The method defined in claim 2; further comprising the steps of passing said cream after separation from said whole milk along a cream path separate from the skim-milk path and withdrawing said variable portion from said cream path.

7. The method defined in claim 6; further comprising the step of maintaining both of said paths under substantially constant pressure.

8. The method defined in claim 6; further comprising the step of maintaining both of said paths under substantially the same constant pressure.

9. The method defined in claim 6; further comprising the steps of:
   measuring in said cream path at a location downstream from the place at which said portion is withdrawn the density of said cream and producing a cream output corresponding to the measure density of said cream;
   introducing into said cream path at a mixing location downstream of the measuring location in said cream path a variable portion of said mixture and mixing same with said cream; and
   comparing said cream output and said mixture output and varying the size of said variable portion of said mixture in dependence on the variation between said cream and mixture outputs so as to impart to said cream a given fat content.

10. A method of producing standardized milk from whole milk, said method comprising the steps of:
    separating said whole milk into skim milk and cream;
    passing said skim milk and said cream along respective skim-milk and cream paths without substantial temperature change;
    maintaining a body of substantially pure water at a temperature substantially equal to the temperature in said paths;
    rendering the fat content of said cream in said cream path substantially uniform;
    mesuring at an upstream measuring location in said skim-milk path the density of said skim milk and producing a skim-milk output corresponding to the measured density;
    measuring the density of said body of water at said temperature and producing a water output corresponding to the measured density of said body;
    comparing said water output and said skim-milk output and generating a difference signal corresponding to the percentage of nonfat solids in said skim milk in said skim-milk path;
    introducing into said skim-milk path at a mixing location therein downstream of said measuring location a variable portion of said cream from said cream path and mixing said skim milk with said variable portion;
    measuring at a downstream measuring location downstream of said mixing location the density of the mixture of said skim milk with said variable portion and producing a mixture output corresponding to the measured density of said mixture;
    comparing said mixture output and said skim-milk output and generating a difference signal corresponding to the fat content of said mixture; and
    comparing said signals and varying the size of said variable portion in dependence on the ratio therebetween so as to impart to said mixture a predetermined ratio between fat content and content of nonfat solids.

11. The method defined in claim 10, wherein said body of water is maintained at the same temperature as the temperature in said paths by heat exchange with the liquid in at least one of the paths.

12. The method defined in claim 11, wherein said heat exchange is indirectly effected between said skim milk and said water.

13. The method defined in claim 10; further comprising the step of maintaining the pressure in said skim-milk path substantially constant.

14. The method defined in claim 10, wherein the fat content of said cream is rendered substantially uniform by varying the pressure in said cream path in dependence on the density of said cream in said path and said skim-milk output.

* * * * *